(12) United States Patent
Juergens

(10) Patent No.: US 11,213,193 B2
(45) Date of Patent: Jan. 4, 2022

(54) ENDOSCOPY SYSTEM AND LIGHT SOURCE OF AN ENDOSCOPY SYSTEM

(71) Applicant: OLYMPUS WINTER & IBE GMBH, Hamburg (DE)

(72) Inventor: Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 309 days.

(21) Appl. No.: 16/466,083

(22) PCT Filed: Nov. 8, 2017

(86) PCT No.: PCT/EP2017/078617
§ 371 (c)(1),
(2) Date: Jun. 3, 2019

(87) PCT Pub. No.: WO2018/108394
PCT Pub. Date: Jun. 21, 2018

(65) Prior Publication Data
US 2020/0060533 A1    Feb. 27, 2020

(30) Foreign Application Priority Data
Dec. 16, 2016   (DE) .................. 102016124730.8

(51) Int. Cl.
*A61B 1/00*   (2006.01)
*A61B 1/07*   (2006.01)
(Continued)

(52) U.S. Cl.
CPC ............ *A61B 1/07* (2013.01); *A61B 1/00117* (2013.01); *A61B 1/045* (2013.01); *A61B 1/063* (2013.01); *A61B 1/0684* (2013.01)

(58) Field of Classification Search
CPC ....... A61B 1/07; A61B 1/00117; A61B 1/045; A61B 1/063; A61B 1/0684; A61B 1/128;
(Continued)

(56) References Cited

U.S. PATENT DOCUMENTS 6,389,205 B1 *  5/2002  Muckner ............ A61B 1/00117
                                               362/574
6,464,633 B1   10/2002  Hosoda et al.
(Continued)

FOREIGN PATENT DOCUMENTS

DE    10 2010 013 307 A1    9/2011
DE    10 2013 113 511 A1    6/2015
(Continued)

OTHER PUBLICATIONS

International Search Report and Written Opinion dated Feb. 26, 2018 received in PCT/EP2017/078617.
(Continued)

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscopy system including: an endoscope; a light source; an optical cable connecting the light source to the endoscope; wherein the endoscope includes at least one bundle of endoscope optical fibers; the cable includes at least one bundle of cable optical fibers; a light source coupling point provided where light is coupled into the cable optical fibers; an endoscope coupling point provided where light is coupled from the cable optical fibers into the endoscope optical fibers; and the light source is configured to selectively illuminate individual cable optical fibers or groups of cable optical fibers at the light source coupling point, the light source including a controller to control the
(Continued)

light source such that at least some of the cable optical fibers not coupled to endoscope optical fibers at the endoscope coupling point are not illuminated by the light source.

8 Claims, 6 Drawing Sheets

(51) Int. Cl.
  *A61B 1/045* (2006.01)
  *A61B 1/06* (2006.01)
(58) Field of Classification Search
  CPC ............ A61B 1/00167; A61B 1/00062; A61B 1/00009; A61B 1/00057; A61B 1/00126; A61B 1/0669; G02B 23/2469; G02B 26/0833
  USPC .......................................... 385/117; 600/178
  See application file for complete search history.

(56) References Cited

U.S. PATENT DOCUMENTS

| | | | |
|---|---|---|---|
| 6,503,196 B1 | 1/2003 | Kehr | |
| 10,209,438 B2 | 2/2019 | Baumann | |
| 2002/0156349 A1 | 10/2002 | Yamaki et al. | |
| 2003/0076571 A1* | 4/2003 | MacAulay | G02B 23/2453 359/237 |
| 2005/0240080 A1* | 10/2005 | Diekmann | A61B 1/00167 600/182 |
| 2011/0257483 A1 | 10/2011 | Mizuyoshi et al. | |
| 2011/0257484 A1* | 10/2011 | Mizuyoshi | G02B 23/2453 600/178 |
| 2012/0019821 A1* | 1/2012 | Chen | G02B 21/0032 356/303 |
| 2013/0162775 A1* | 6/2013 | Baumann | G01S 17/894 348/45 |
| 2014/0114196 A1* | 4/2014 | Kamimura | A61B 5/0084 600/478 |
| 2014/0210975 A1* | 7/2014 | Hirakawa | G02B 23/26 348/68 |
| 2015/0185414 A1* | 7/2015 | Baumann | A61B 1/00006 362/553 |

FOREIGN PATENT DOCUMENTS

| | | |
|---|---|---|
| JP | 2001-059942 A | 3/2001 |
| JP | 2011-224042 A | 11/2011 |
| WO | 99/16341 A1 | 4/1999 |

OTHER PUBLICATIONS

German Office Action dated Nov. 15, 2017 received in 10 2016 124 730.8.

Japanese Office Action dated Jul. 28, 2020 in Japanese Patent Application No. 2019-531264.

* cited by examiner

ENDOSCOPY SYSTEM AND LIGHT SOURCE OF AN ENDOSCOPY SYSTEM

CROSS-REFERENCE TO RELATED APPLICATION

The present application is based upon and claims the benefit of priority from PCT/EP2017/078617 filed on Nov. 8, 2017, which claims benefit to DE 10 2016 124 730.8 filed on Dec. 16, 2016, the entire contents of each of which are incorporated herein by reference.

BACKGROUND

Field

The present disclosure relates to an endoscopy system with an endoscope, a light source and an optical cable connecting the light source to the endoscope, wherein the endoscope comprises at least one bundle of endoscope optical fibers, the cable comprises at least one bundle of cable optical fibers, a light source coupling point is provided at which light of the light source is coupled into the at least one bundle of cable optical fibers, and an endoscope coupling point is provided at which light of the light source is coupled from the at least one bundle of cable optical fibers into the at least one bundle of endoscope optical fibers. The present disclosure further relates to a light source of a corresponding endoscopy system.

Prior Art

For some time, corresponding endoscopy systems have been used successfully for optical examination of cavities that are difficult to access in technical installations or in animal or human patients. In these cases, the endoscope is used to capture an image of the inner surface of the cavity and to make this image available outside of the cavity. The illumination is generally provided via endoscope optical fibers extending through the interior of the endoscope. In many cases, the light source used for illumination is configured as a separate appliance, and the light is then conveyed to the endoscope optical fibers via cable optical fibers routed through an optical cable.

At the light source, the light is coupled into the optical cable at a light source coupling point. For this purpose, the optical cable is introduced into a socket of the light source such that the ends of the cable optical fibers are arranged in a plane that is illuminated by the light source. The connection of the light source to the optical cable is generally releasable.

At the endoscope, the light is coupled from the cable optical fibers into the endoscope optical fibers at an endoscope coupling point. For this purpose, the ends of the endoscope optical fibers and of the cable optical fibers are arranged at the shortest possible distance from each other, and a fiber cone can be provided here to adapt the numerical aperture of the respective fibers. The connection of the optical cable to the endoscope can be fixed or releasable.

The spatial separation of the light source from the endoscope reduces the heating of the endoscope through heat losses of the light source. However, coupling losses at the endoscope coupling point also lead to heating of the endoscope, which is undesirable for various reasons. This effect is heightened by the fact that newer generations of endoscopes require more light on account of higher optical resolution and larger viewing fields.

An endoscopy system according to the prior art is shown in FIG. 1. The endoscopy system comprises an endoscope 1, an optical cable 2 and a light source 3.

The endoscope 1 has a shaft 11, a main body 12 and an eyepiece cup 13. An objective 14 is arranged at the distal end of the shaft 11. The objective 14 generates an image of a structure S of interest, which image is transported by an optical image carrier 15 through the main body 12 into the eyepiece cup 13. There, the image is presented through the eyepiece 16 such that it can be viewed by a user looking through the eyepiece cup 13 into the endoscope 1. Endoscope optical fibers 17 are routed through the endoscope 1 and terminate proximally at a fiber cone 19 in a light-guiding connector piece 18. The endoscope optical fibers terminate distally at the end of the shaft 11.

The optical cable 2 connects the endoscope 1 to the light source 3. The optical cable 2 comprises a first plug 50, which is plugged onto the light-guiding connector piece 18 of the endoscope 1, and a second plug 51, which is plugged into the light source 3. For the sake of clarity, cable optical fibers 52 running through the optical cable 2 are shown only in the region of the plugs 50, 51. The transition from the optical cable 2 to the fiber cone 19 in the light-guiding connector piece 18 forms an endoscope coupling point. The end faces of the cable optical fibers 52 in the second plug 51 form a light source coupling point.

The light source 3 comprises a light-emitting means 61, of which the light is focused by a collimator 62 onto the end faces of the cable optical fibers. The light-emitting means 61 can be, for example, a xenon high-pressure lamp or a powerful light-emitting diode.

To improve ergonomics and for documentation purposes, direct viewing through the endoscope 1 is in most cases dispensed with these days. Instead, a camera head 20 is mounted on the eyepiece cup 13, and an objective 21 and an image sensor 22 (such as a CCD or CMOS) are in turn arranged in the camera head 20. The image of the structure S is imaged through the objective 21 onto the image sensor 22 and is converted by the latter into a video signal, which is transmitted via a cable 23 to a camera control unit 30. The camera head 20 can have a focusing device 24.

The camera control unit comprises a video processor 31 with which the video signal coming from the camera head 20 is processed for display on a monitor 40 and/or for recording on a storage device 41. The camera control unit further comprises a control unit 32 for generating control signals for the image sensor 22. The camera control unit 30 further comprises an image-evaluating device 33, which evaluates the received video image in terms of various criteria. Thus, the image-evaluating unit 33 can evaluate the image definition and send a signal to the focusing device 24 so as to move the objective 21 in order to improve the image definition. The image-evaluating unit 33 can also evaluate the brightness and/or the contrast of the image and send a signal to the control unit 32 so as to change the exposure time of the image sensor 22. Moreover, the image-evaluating unit 33 can send a signal to the light source 3 in order to adapt the illumination intensity.

It will be noted that the end face of the cable optical fibers in the plug 50 is slightly larger than the end face of the fiber cone 19. This is because the cable 2 can be used not just with the endoscope 1 but also with other types of endoscope that have more endoscope optical fibers and thus also have a larger fiber cone. Therefore, the end face of the cable optical fibers is dimensioned such that, in all endoscope types, the fiber cone is fully illuminated. Light conveyed through cable optical fibers 52 of which the end face is arranged outside the cross section of the fiber cone 19 is absorbed in the light-guiding connector piece 18 and therefore leads to heating of the endoscope 1.

SUMMARY

An object is therefore to make available an endoscopy system and a light source that are improved in respect of the problems described.

According to an embodiment, such object is achieved by an endoscopy system with an endoscope, a light source and an optical cable connecting the light source to the endoscope, wherein the endoscope comprises at least one bundle of endoscope optical fibers, the cable comprises at least one bundle of cable optical fibers, a light source coupling point is provided at which light of the light source is coupled into the at least one bundle of cable optical fibers, and an endoscope coupling point is provided at which light of the light source is coupled from the at least one bundle of cable optical fibers into the at least one bundle of endoscope optical fibers, the light source is configured to selectively illuminate individual cable optical fibers or groups of cable optical fibers at the light source coupling point, and the light source is assigned a controller which is able to control the light source in such a way that only or predominantly the cable optical fibers that are coupled to endoscope optical fibers at the endoscope coupling point are illuminated in a targeted manner.

The expression "groups of cable optical fibers" within the context of the present disclosure is understood to mean groups of cable optical fibers that comprise more than one cable optical fiber and less than all the cable optical fibers, for example less than 20%, such as less than 2% of all the cable optical fibers of the optical cable. Alternatively, a group of cable optical fibers can also comprise approximately 3 to 20, 10 to 100 or 20 to 200 cable optical fibers. Within the context of the present disclosure, cable optical fibers are regarded as being coupled to endoscopy optical fibers in the case where the light coupled from the light source into the cable optical fibers is coupled into one or more endoscope optical fibers with a sufficient coupling efficiency, for example of at least 50%, such as of at least 75%.

The present disclosure recognizes that not every cable optical fiber lies opposite an endoscope optical fiber at the endoscope coupling point. Positioning errors and differences in diameter between the coupled fiber bundles have the effect that light from some cable optical fibers is radiated on the side of the endoscope optical fibers, for example, onto fillers or metal mounts, and is absorbed there. In this way, the endoscope is unnecessarily heated in the region of the endoscope coupling point.

In an endoscopy system according to an embodiment, the heating of the endoscope can be considerably reduced by the fact that the cable optical fibers not coupled to the endoscope optical fibers are not illuminated by the light source.

According to an embodiment, the light source can be configured to selectively illuminate individual positions of a predefined position grid at the light source coupling point, and the controller can be assigned a memory which, for the individual positions of the position grid, stores information as to whether a cable optical fiber to be illuminated is located at the respective position. The position grid can be, for example, an orthogonal or hexagonal grid. Alternatively, it can be a concentric or spiral-shaped polar grid.

The light source can comprise at least one movable mirror with which the light of the light source can be deflected in the direction of the respective positions of the position grid. The at least one mirror can be a digital micromirror device (DMD).

Individual positions of the position grid can be selectively illuminated in an uncomplicated way by using at least one movable mirror, such as by using DMDs. An individual, fixed light source can be used, of which the light is then deflected by the at least one movable mirror onto the respective position that is to be illuminated. Therefore, it is not necessary to provide a dedicated light source for each individual position. When using a DMD, an individual light source can also generate a collimated light beam whose diameter is adapted to illuminate all the positions that are to be illuminated. For each position that is to be illuminated, the DMD can have a micromirror, which deflects part of the light beam either in the direction of the position to be illuminated or in the direction of an absorber.

In another embodiment, the light source can comprise a light-emitting diode or a laser diode. Such light sources are long-lasting and can be switched on and off with sufficient speed to permit sequential illumination of the individual positions of the position grid.

In a variation, individual endoscope optical fibers of the at least one bundle of endoscope optical fibers can be arranged in the endoscope in such a way that they radiate light in different directions, and, for individual positions of the position grid, the memory of the controller stores information concerning the direction in which light is radiated from an endoscope optical fiber coupled to a cable optical fiber that is arranged at the corresponding position. In this variation, it is additionally possible for the light to be output in a targeted manner only or into those endoscope optical fibers that radiate said light in a desired direction. In this way, individual regions of the cavity to be examined can be more weakly or more strongly illuminated, for example in order to emphasize certain structures or to reduce disruptive reflection.

The endoscope can have a variable viewing direction. Illumination light can then be radiated in the direction corresponding to the viewing direction that has been set on the endoscope.

The endoscopy system can comprise an image-capturing device for capturing images generated by the endoscope and an image-evaluating device for evaluating the images captured by the image-capturing device, wherein the image-evaluating device and the controller are coupled to each other and are configured to determine whether a cable optical fiber coupled to an endoscope optical fiber at the coupling point is located at a position illuminated by the light source, and/or in which direction light is radiated from an endoscope optical fiber which is coupled to a cable optical fiber arranged at the corresponding position.

In this regard, at coupling points where an optical cable is coupled releasably to an endoscope or to a light source, it may happen that, after each connection process, different optical fibers may be arranged at a defined position, such that the positions of the position grid that are to be illuminated can be ascertained only after all the components have been connected. In a suitably configured endoscopy system, the light source can, for example, illuminate a defined position of the position grid in a targeted manner, while the endoscope is oriented toward an object, for example a reference card. By way of the image-capturing device and the image-evaluating device, it is then determined whether, and possibly to what extent, the illumination of the defined positions leads to an increase in the brightness of the captured image, and at what place on the image the brightness is increased. It is thus possible to determine whether the cable optical fiber arranged at the respective position is effectively coupled to an endoscope optical fiber, and how great the coupling efficiency is. It is likewise possible to obtain information concerning the direction of radiation of the coupled endoscope optical fibers. The information thus obtained is then stored in the memory for the respectively illuminated position.

In another embodiment, the endoscopy system can be provided either to operate in an observation mode, in which the only positions of the position grid that are illuminated in a targeted manner are those where cable optical fibers are located which are coupled to endoscope optical fibers at the coupling point, and/or where cable optical fibers are located which at the coupling point are coupled to endoscope optical fibers that radiate light in a desired direction, or to operate in a determination mode, in which positions of the position grid are illuminated simultaneously or sequentially, wherein the image-capturing device, the image-evaluating device and the controller interact in order to establish whether, at the respectively illuminated positions of the position grid, cable optical fibers are arranged which are coupled at the coupling point to endoscope optical fibers, and, if appropriate, in which direction light is radiated from these endoscope optical fibers.

It is thereby possible for the endoscopy system to be switched, as and when required, between the observation mode and the determination mode.

Such object is further achieved by a light source of an endoscopy system that is configured in accordance with the above embodiments.

BRIEF DESCRIPTION OF THE DRAWINGS

The embodiments are explained in more detail below on the basis of a number of examples in the drawings, in which.

DETAILED DESCRIPTION

Figure 1:
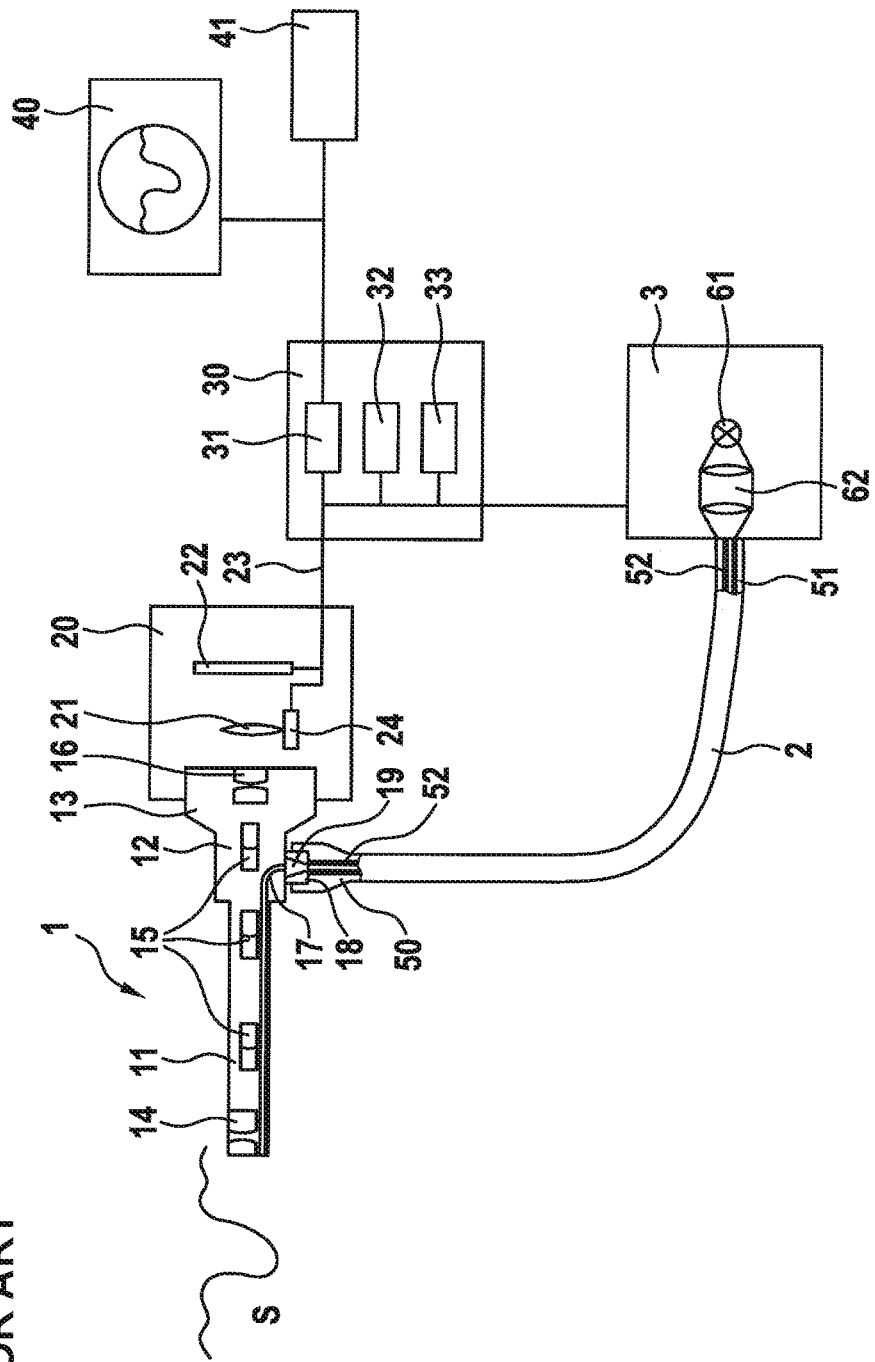
FIG. 1 illustrates an endoscopy system according to the prior art.
Figure 2:
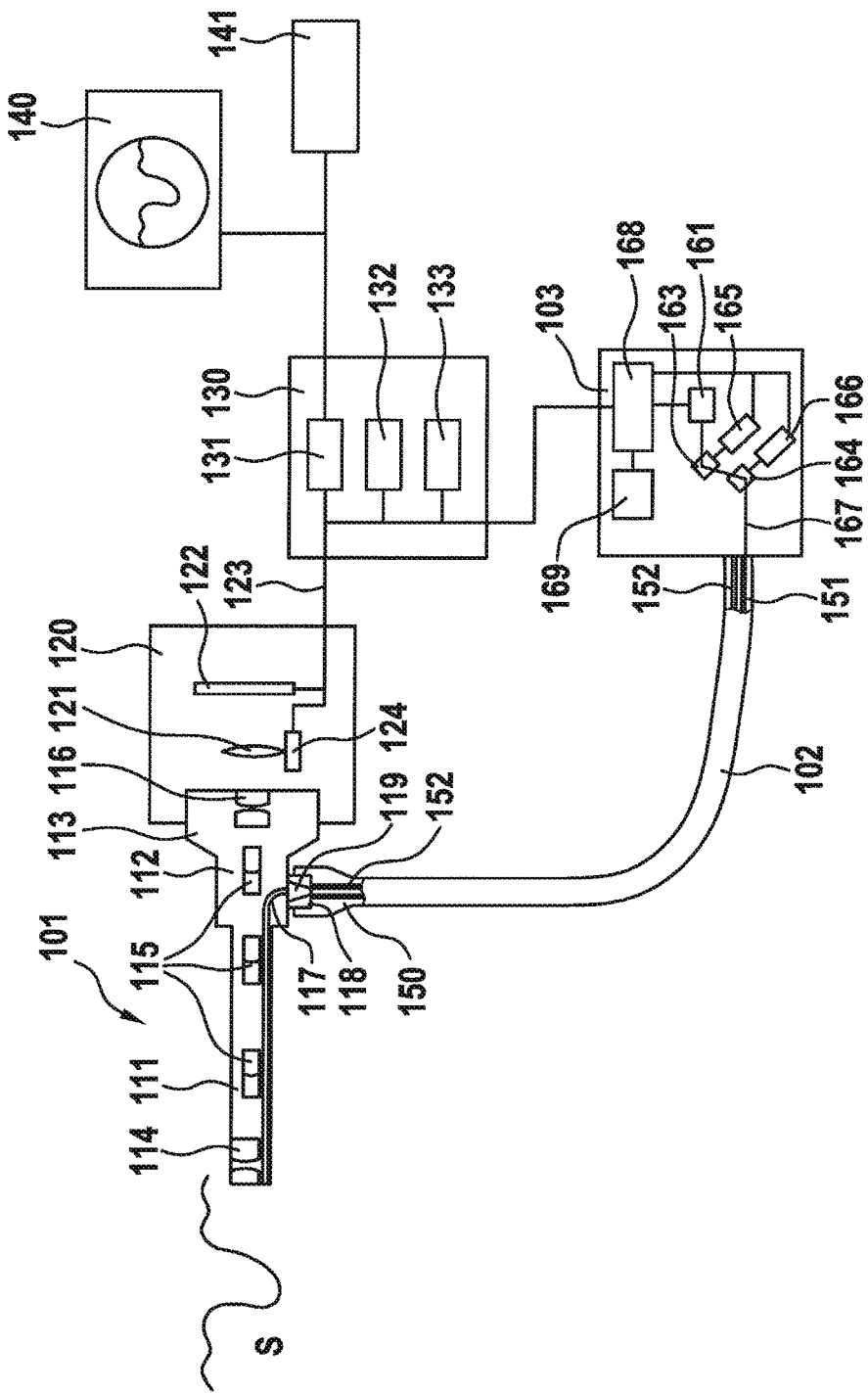
FIG. 2 illustrates an endoscopy system according to one aspect.

FIG. 2 shows a modified endoscopy system. The endoscopy system again comprises an endoscope 101, an optical cable 102 and a light source 103. FIG. 2 likewise shows a camera head 120, a camera controller 130, a monitor 140 and a recording appliance 141. Insofar as the structure and function of the components shown in FIG. 2 correspond to the corresponding components in FIG. 1, they are not described again here. These components are then provided with a reference sign increased by 100 (e.g., image sensor 22 of FIG. 1 is illustrated as image sensor 122 in FIG. 2).

The light source 103 comprises a light-emitting means 161 which, in the example shown, is a laser diode or a white light LED with collimator. The light beam 167 of the light-emitting means 161 is deflected by two swivel mirrors 163, 164 in the direction of the end face of the cable optical fibers 150. The swivel mirrors 163, 164 are driven by micromotors 165, 166 such that the light beam 167 sweeps over individual positions of the end face of the cable optical fibers 152 according to a predefined pattern. The micromotors 165, 166 are actuated via a controller 168. The controller 168 moreover switches the light-emitting means 161 on when the light beam is directed to a cable optical fiber 152 which lies opposite the fiber cone 119 at the endoscope coupling point and is thus coupled to an endoscope optical fiber 117. By contrast, the controller 168 switches the light-emitting means 161 off when the light beam is directed to a cable optical fiber 152 which does not lie opposite the fiber cone 119 at the endoscope coupling point and is thus not coupled to an endoscope optical fiber 117. Heating of the endoscope 101 by light absorbed in the light-guiding connector piece 118 is thus considerably reduced.

Depending on the beam cross section of the light beam 167 and the cross section of the cable optical fibers 153, the light beam 167 can also illuminate a group of cable optical fibers simultaneously. Such a group can comprise, for example, less than 20% of all the cable optical fibers, or less than 2% of all the cable optical fibers. A group can consist of 3 to 20, 10 to 100 or 20 to 200 cable optical fibers.

The controller 168 is assigned a memory 169 which stores data of a predefined position grid over which the light beam 167 travels. Different position grids are shown in FIGS. 3a to 3d.

Figure 3A:
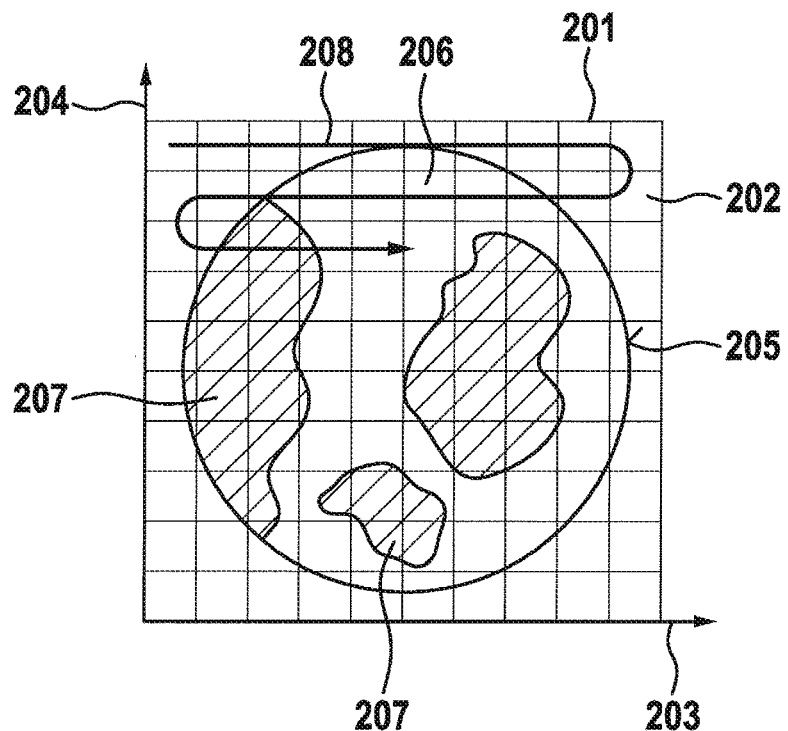
FIGS. 3a-3d illustrate different position grids.

FIG. 3a shows an orthogonal position grid 201 in which rectangular cells, such as square cells 202, are arranged without gaps. Each cell 202 is defined by its position with respect to two axes 203, 204 lying at right angles to each other. The end face 205 of the bundle of cable optical fibers 152 that are arranged in the light source coupling point is indicated within the grid 201. The cable optical fibers 152 that are coupled to endoscope optical fibers 117 and the cable optical fibers that are not coupled to endoscope optical fibers 117 lie next to one another in an unsorted manner in the end face, since the cable optical fibers are routed in an unsorted manner in the optical cable 102. However, it will be noted that the end face has regions 206 in which coupled cable optical fibers dominate and regions 207 in which uncoupled cable optical fibers dominate. This is on account of the process of manufacture of the optical cable 102, which process will not however be discussed in any detail here. The regions 207 are indicated by hatching in FIG. 3a.

For improved clarity, the position grid 201 is shown in FIG. 3a with very low position resolution. In actual fact, the position resolution chosen will be at least so high that the surface area of individual cells 202 corresponds approximately to the cross section of a cable optical fiber 152 or of a small group of cable optical fibers 152.

Figure 3B:
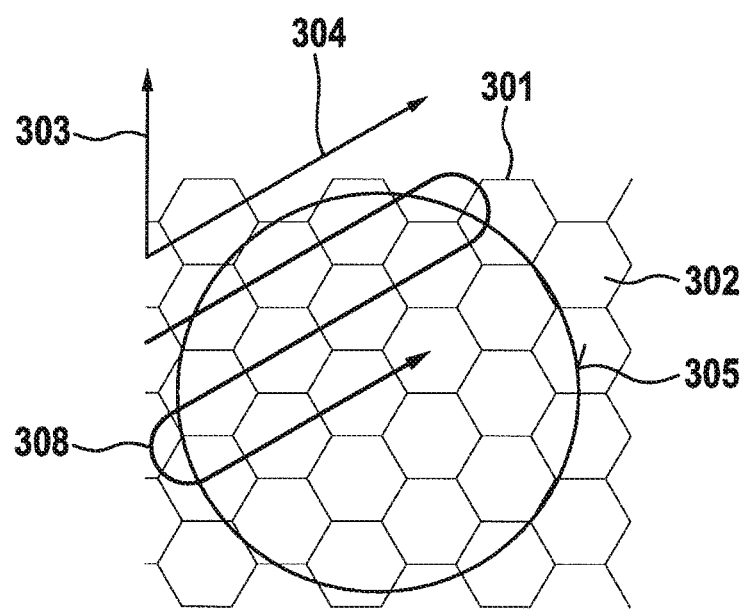

FIG. 3b shows an alternative embodiment of a position grid 301, which is in this case a hexagonal grid. The cells 302 are shaped as uniform hexagons and are arranged free of gaps in the grid 301. Each cell is clearly defined by its position with respect to two axes 303, 304, wherein the axes 303, 304 are arranged at an angle of 60° to each other. The end face 305 of the bundle of cable optical fibers 152 that are arranged in the light source coupling point is once again indicated within the grid 301.

The hexagonal arrangement of the cells 302 in the position grid 301 is suitable for simulating the actual position of the cable optical fibers 152, since the cable optical fibers 152 generally have a round cross section and can likewise be arranged for the most part hexagonally when packed tightly.

Figure 3C:
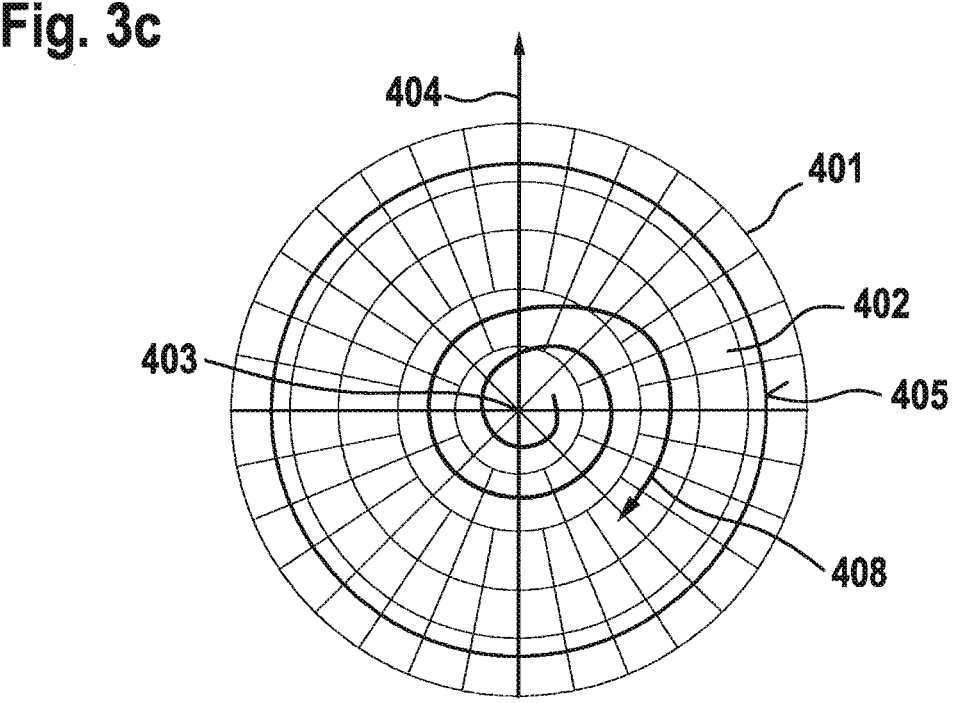

FIG. 3c shows an alternative position grid 401 with a concentrically polar structure. The cells 402 are each configured as ring segments. In contrast to the position grids 201, 301, the individual cells 402 of the position grid 401 are not fully congruent to each other. Each cell 402 is clearly defined by its distance from the center point 403 of the position grid and by its angle to a reference axis 404. In order to ensure an approximately identical surface area of all the cells 402, the angle resolution of the position grid 401 can be enhanced as the distance from the center point 403 increases.

Once again, the end face 405 of the bundle of cable optical fibers 152 that are arranged in the light source coupling point is indicated within the grid 401.

The concentric arrangement of the cells 402 in the position grid 401 is suitable for imaging the generally round cross section of the optical cable 103.

Figure 3D:
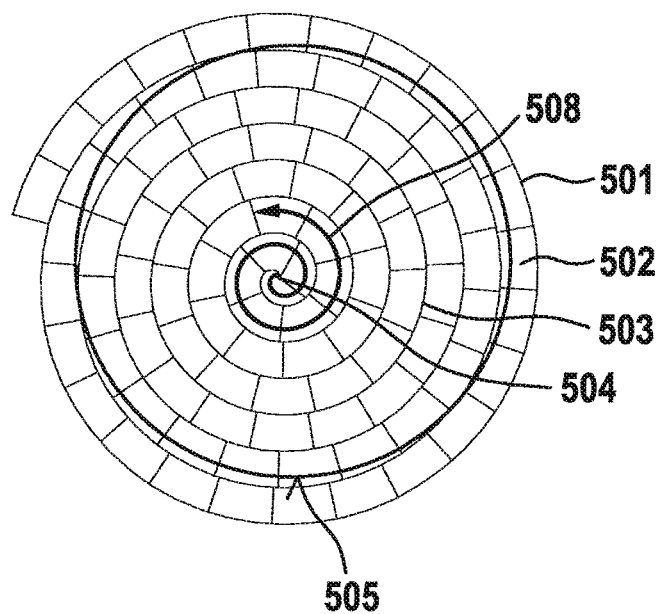

FIG. 3d shows a further alternative embodiment of the position grid 501 with a spiraling polar structure. The cells 502 are arranged along a spiraling line 503 which starts out from the center point 504 of the position grid 501. The length of all the cells 502 is approximately identical in the direction of the line 503. In contrast to the position grids 201, 301 and 401, each cell 502 of the position grid 501 is clearly defined solely by its position along the line 503.

Once again, the end face 505 of the bundle of cable optical fibers 152 that are arranged in the light source coupling point is indicated within the grid 501.

The structure of the position grid 501 is, like that of the position grid 401, suitable for imaging the cross section of the optical cable 103. Moreover, this structure can be traveled across easily by movement of the swivel mirrors 163, 164.

As regards the position resolution, the comments already made above in respect of position grid 201 also apply to position grids 301, 401 and 501.

For each cell 202, 302, 402, 502 of the position grids 201, 301, 401, 501, i.e. for every position, the memory 169 now stores information concerning whether, and if appropriate with what coupling efficiency, a cable optical fiber arranged at the respective position is coupled to an endoscope optical fiber. Depending on this information, the controller 168 switches the light-emitting means 161 on or off.

The light beam 167 travels across the position grid 201, 301 line by line, wherein the scanning direction can be reversed between two lines. The light beam 167 then moves in a meandering formation across the respective position grid. The position grid 401 can be traveled across in rings, wherein the direction of travel remains the same for all the rings. The position grid 501 is accordingly traveled in a spiral shape. This is represented in each case by the arrows 208, 308, 408, 508.

Figure 4:
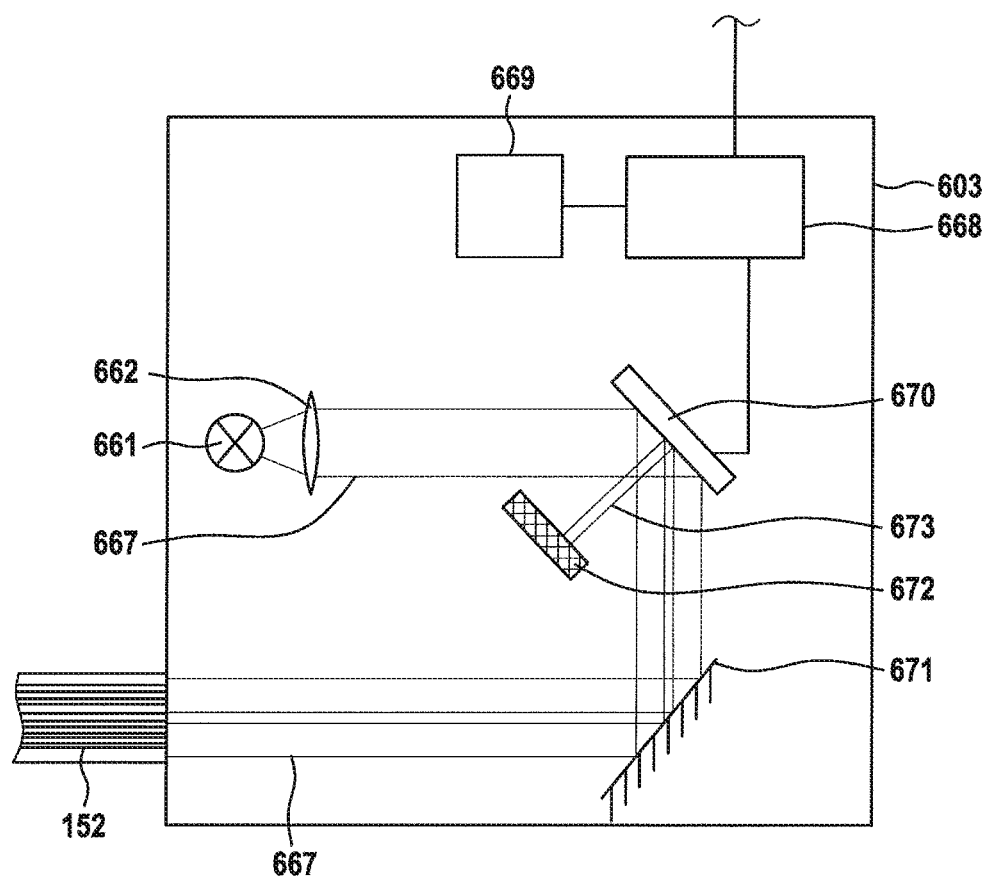
FIG. 4 illustrates a light source according to an embodiment.

FIG. 4 shows a light source 603 which can be used instead of the light source 103 in the endoscopy system shown in FIG. 2.

The light source 603 comprises a light-emitting means 661, for example a high-power white light LED, to which a collimator 662 is assigned. The light issuing from the light-emitting means is shaped by the collimator 662 into a parallel beam bundle 667. The beam bundle is reflected onto the end face of the cable optical fibers 152 via a DMD 670 and a plane mirror 671.

The DMD 670 is composed of a large number of micromirrors which are arranged in a rectangular grid and can be tilted individually by means of controllable actuators. The DMD is oriented in such a way that the micromirrors in the basic state reflect the beam bundle 667 in the direction of the mirror 671. A controller 668 is configured to actuate individual micromirrors of the DMD 670 such that they reflect the beam bundle 667 onto the absorber 672 instead of onto the mirror 671. This is shown for a part beam 673. The light of the part beam 673 is thus masked from the beam bundle 667, and a cable optical fiber 152 arranged at the corresponding position is not illuminated.

The light source 603 shown in FIG. 4 can operate with a position grid as shown in FIG. 3a. Compared to the light source 103, the light source 603 has the advantage that several positions of the position grid can be illuminated in parallel. A rapid movement of a light beam is therefore not necessary. Similarly, the light-emitting means 661 does not have to be switched on and off at a high clock rate. The information concerning which micromirrors of the DMD have to be deflected is once again stored in a memory 669.

Figure 5:
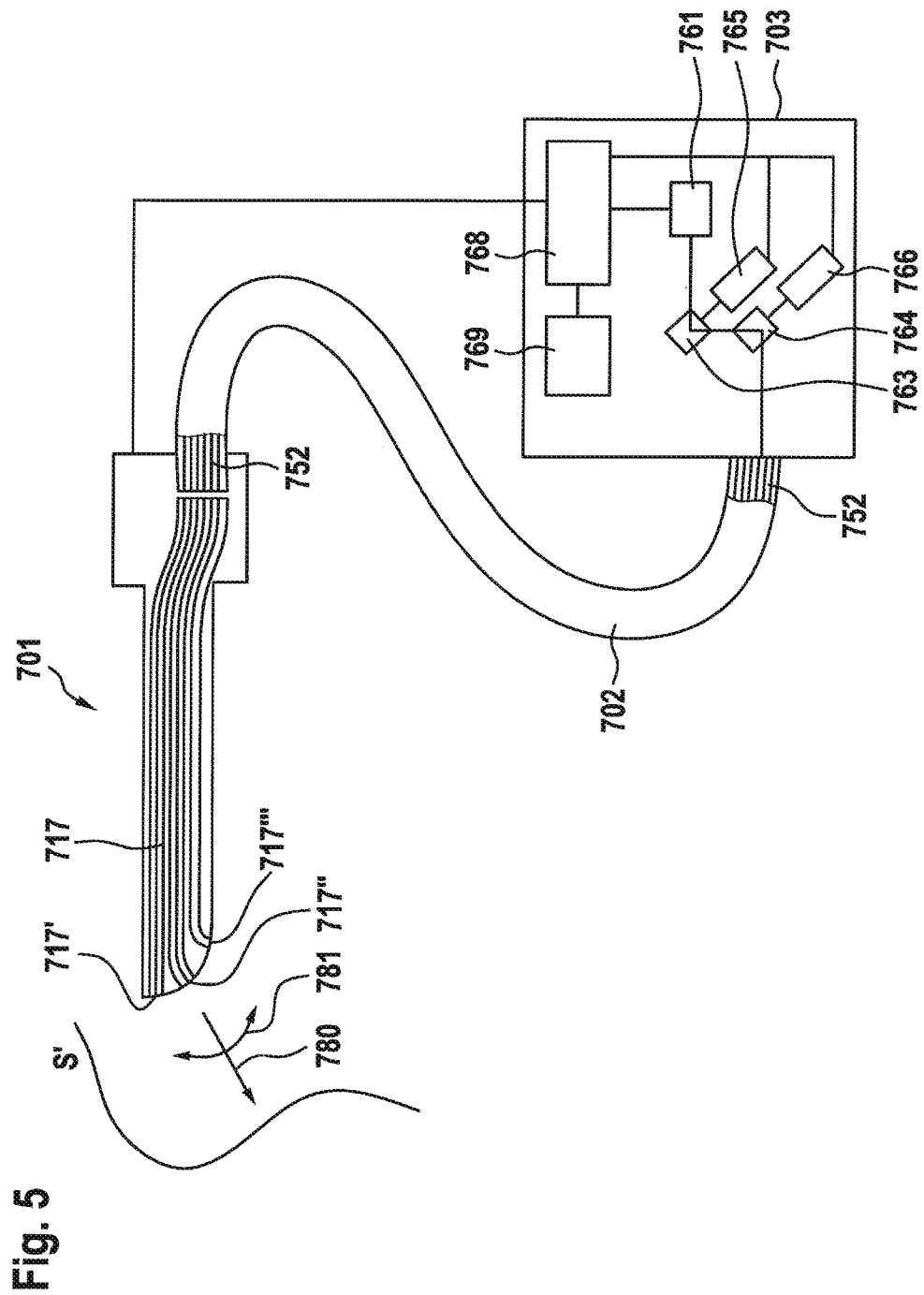
FIG. 5 illustrates an endoscopy system according to a further aspect.

FIG. 5 shows a further configuration of an endoscopy system with an endoscope 701, an optical cable 702 and a light source 703.

In the configuration shown here, the endoscope has a variable viewing direction, wherein the viewing direction indicated by the arrow 780 can be pivoted along the double arrow 781. With such an endoscope 701, extensive structures S' are able to be observed effectively without the entire endoscope 701 having to be moved. For reasons of clarity, the imaging elements of the endoscope 701 are not shown here.

At the distal end of the endoscope 701, the endoscope optical fibers 717 routed through the endoscope 701 are divided into three partial bundles 717', 717", 717''' which are oriented in different directions. Depending on the orientation of the viewing direction of the endoscope 701, illumination light is mainly required only from one of the partial bundles 717', 717", 717'''. The orientation of the viewing direction is transmitted by the endoscope 701 to the controller 768 of the light source 703. In addition to the information concerning the coupling or the coupling efficiency of the cable optical fibers 752 arranged at the position in question, the memory 769 also stores, for each position of the position grid, information concerning the direction of radiation of the endoscope optical fibers 717 coupled to the corresponding cable optical fibers 752.

The controller 768 can thus control the light-emitting means 761 and the micromirrors 765, 766 of the swivel mirrors 763, 764 such that the only cable optical fibers that are illuminated are the ones that are coupled to endoscope optical fibers oriented in the desired direction of radiation.

The information to be stored in the memory is in most cases ascertained only after an endoscopy system has been put together ready for use. In order to determine the information, the endoscope of the endoscopy system is oriented with respect to a reference object which, for example, may be a calibration card. Thereafter, the endoscopy system is switched to a determination mode in which all the positions of the position grid are illuminated in succession by the light source, and the change in the brightness of the image captured by the endoscope is determined. The image brightness determined upon illumination of one position is used as a measure of the coupling efficiency of a cable optical fiber to an endoscope optical fiber at the position in question and is stored in the memory. It is also possible to illuminate each position several times and to use the mean value of the determined image brightness values.

If information is additionally to be obtained concerning the direction of radiation of the coupled endoscope optical fibers, then, in addition to the absolute image brightness, the location of maximum brightness in the image is also determined and stored in the memory as a measure of the direction of radiation. If the endoscopy system comprises an endoscope with an adjustable viewing direction, the determination has to be carried out for the different viewing directions set.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscopy system comprising:
an endoscope;
a light source; and
an optical cable connecting the light source to the endoscope; wherein
the endoscope comprises at least one bundle of endoscope optical fibers;
the cable comprises at least one bundle of cable optical fibers;
a light source coupling is provided where light of the light source is coupled into the at least one bundle of cable optical fibers;
an endoscope coupling is provided where light of the light source is coupled from the at least one bundle of cable optical fibers into the at least one bundle of endoscope optical fibers;
the light source is configured to selectively illuminate individual cable optical fibers or groups of cable optical fibers at the light source coupling, the light source comprising a controller configured to control the light source such that at least some of the cable optical fibers not coupled to endoscope optical fibers at the endoscope coupling are not illuminated by the light source;
the light source is configured to selectively illuminate individual positions of a predefined virtual position grid arranged to a surface of the light source coupling, and the controller is assigned a memory which, for the individual positions of the predefined virtual position grid, stores information as to whether a cable optical fiber to be illuminated is located at the respective position; and
the endoscopy system comprises an image sensor for capturing images generated by the endoscope, and a camera controller configured to evaluate the images captured, wherein the camera controller and the controller are coupled to each other and are configured to determine, based on the evaluation of the captured images, whether one or more of a cable optical fiber coupled to an endoscope optical fiber at the coupling point is located at a position illuminated by the light source, and in which direction light is radiated from an endoscope optical fiber which is coupled to a cable optical fiber arranged at a corresponding position.

2. The endoscopy system as claimed in claim 1, wherein the light source comprises at least one movable mirror with which the light of the light source can be deflected in a direction of respective positions of the predefined virtual position grid.

3. The endoscopy system as claimed in claim 2, wherein the at least one movable mirror is a digital micromirror device.

4. The endoscopy system as claimed in claim 1, wherein the light source comprises one of a light-emitting diode and a laser diode.

5. The endoscopy system as claimed in claim 1, wherein individual endoscope optical fibers of the at least one bundle of endoscope optical fibers are arranged in the endoscope such that the individual endoscope optical fibers radiate light in different directions, and, for individual positions of the predefined virtual position grid, the memory of the controller stores information concerning the direction in which light is radiated from an endoscope optical fiber coupled to a cable optical fiber that is arranged at a corresponding position.

6. The endoscopy system as claimed in claim 5, wherein the endoscope has a variable viewing direction.

7. The endoscopy system as claimed in claim 1, wherein the endoscopy system is provided either to operate in an observation mode, in which the only positions of the predefined virtual position grid that are illuminated by the light source are those where cable optical fibers are located which are coupled to endoscope optical fibers at the coupling point, and/or where cable optical fibers are located which at the coupling point are coupled to endoscope optical fibers that radiate light in a desired direction, or to operate in a determination mode, in which all positions of the predefined virtual position grid are illuminated, wherein the image sensor, the camera controller and the controller interact in order to establish whether, at the respectively illuminated positions of the position grid, cable optical fibers are arranged which are coupled at the coupling point to endoscope optical fibers, and, if appropriate, in which direction light is radiated from the coupled endoscope optical fibers.

8. An endoscopy system comprising:
an endoscope;
a light source; and
an optical cable connecting the light source to the endoscope; wherein
the endoscope comprises at least one bundle of endoscope optical fibers;
the cable comprises at least one bundle of cable optical fibers;
a light source coupling is provided where light of the light source is coupled into the at least one bundle of cable optical fibers;
an endoscope coupling is provided where light of the light source is coupled from the at least one bundle of cable optical fibers into the at least one bundle of endoscope optical fibers;
the light source is configured to selectively illuminate individual cable optical fibers or groups of cable optical fibers at the light source coupling, the light source comprising a controller configured to control the light source such that at least some of the cable optical fibers not coupled to endoscope optical fibers at the endoscope coupling are not illuminated by the light source; and
the light source is configured to selectively illuminate individual positions of a predefined virtual position grid arranged to a surface of the light source coupling, and the controller is assigned a memory which, for the individual positions of the predefined virtual position grid, stores information as to whether a cable optical fiber to be illuminated is located at the respective position.

* * * * *